United States Patent [19]
Gletos

[11] Patent Number: 5,508,398
[45] Date of Patent: Apr. 16, 1996

[54] NEW EXTRACTIVE PROCESS FOR THE RECOVERY OF NATURALLY OCCURRING MACROLIDES

[75] Inventor: Constantine Gletsos, Plattsburgh, N.Y.

[73] Assignee: American Home Products Corporation, Madison, N.J.

[21] Appl. No.: 368,675

[22] Filed: Jan. 4, 1995

Related U.S. Application Data

[63] Continuation-in-part of Ser. No. 148,096, Nov. 5, 1993, abandoned.

[51] Int. Cl.$^6$ .................................................. C07D 498/16
[52] U.S. Cl. ................................................................ 540/456
[58] Field of Search ............................................... 540/456

[56] References Cited

U.S. PATENT DOCUMENTS

| | | | |
|---|---|---|---|
| 3,993,749 | 11/1976 | Sehgal et al. | 424/122 |
| 4,894,366 | 1/1990 | Okuhara et al. | 540/456 |
| 5,091,389 | 2/1992 | Ondeyka | 514/291 |

FOREIGN PATENT DOCUMENTS

| | | | |
|---|---|---|---|
| WO93/11130 | 6/1993 | WIPO | C07D 498/18 |

OTHER PUBLICATIONS

Sehgal, Baker and Vezina, J. of Antibiotics, 28(10)727 (1975).

Yohannes, Myers and Danishefsky, Tetrahedron Letters 34(13), 2075–2078 (1993).

Luengo, Konialian and Holt, Tetrahedron Letters 34(6), 991–994 (1993).

Steffan et al., Tetrahedron Letters 34(23), 3699–3702 (1993).

Yohannes and Danishefsky, Tetrahedron Letters 33(49), 7462–7472 (1992).

*Primary Examiner*—Robert T. Bond
*Attorney, Agent, or Firm*—Robert F. Boswell, Jr.

[57] ABSTRACT

This invention relates to a process of recovering a neutral macrolide antibiotic, especially a tricyclic macrolide such as rapamycin from concentrates of fermentation broth extracts or mother liquors whereby acidic and/or basic components formed in the fermentation process are removed by utilizing aqueous base or acid extraction procedures from a water-immiscible solution of said concentrate and non-polar components are separated from the neutral macrolide by selective solubility.

11 Claims, No Drawings

NEW EXTRACTIVE PROCESS FOR THE RECOVERY OF NATURALLY OCCURRING MACROLIDES

This application is a continuation in part of application Ser. No. 08/148,096 filed Nov. 5, 1993.

FIELD OF INVENTION

This invention relates to a process employing simple extractions for separating a naturally occurring neutral non-polypeptide macrolide, especially a tricyclic macrolide such as rapamycin, 32-desmethylrapamycin, 15-deoxorapamycin, FK-506 or naturally occurring homologs, analogs or isomers thereof, from other naturally occurring components that are formed by fermentation processes from certain microorganisms and separated as mixtures from the fermentation broths. This process avoids the costly and time consuming chromatographic separations disclosed in the scientific and patent literature. More specifically, this invention relates to a process for recovering the neutral tricyclic macrolide rapamycin from fermentation broth extract concentrate and from mother liquor concentrates obtained from previous isolation and/or purification procedures. The term "macrolide" used herein refers to neutral non-polypeptide macrolides and includes the tricyclic macrolides such as rapamycin (serolimus) and FK-506 (tacrolimus).

The neutral tricyclic macrolides exemplified by rapamycin and FK-506 have immunosuppressant activity as well as antibiotic and other pharmacological activities and are useful in treating graft and transplant rejections, diseases of inflammation, and autoimmune diseases such as lupus, rheumatoid arthritis, diabetes mellitus and multiple sclerosis.

The tricyclic macrolide rapamycin shown below is a crystalline solid soluble in methanol, acetone, dimethylformamide, slightly soluble in diethyl ether and is sparingly soluble in hexane or petroleum ether and is insoluble in water. The atom numbering system is that used by Chemical Abstracts.

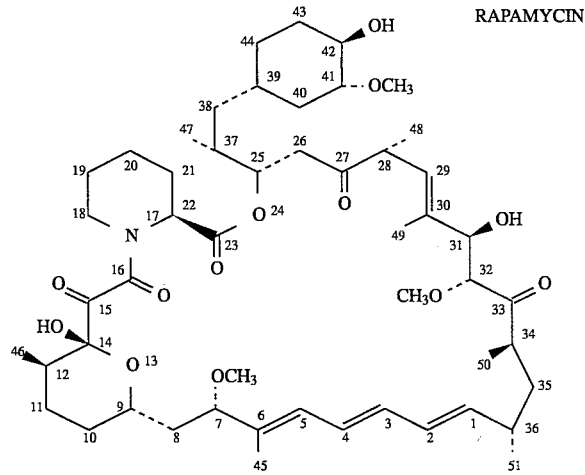

The structures of 32-desmethylrapamycin and 15-deoxorapamycin can easily be discerned from the above structure of rapamycin. The structure of the neutral tricyclic macrolide FK-506 shown below shares many structural features with rapamycin.

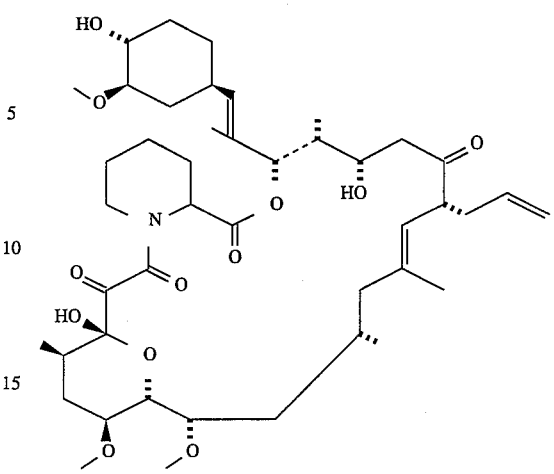

Since the structures of rapamycin and FK-506 and their naturally occurring isomers, analogs or homologs are so similar, it is expected that FK-506 and naturally occurring isomers, analogs or homologs of FK-506 and rapamycin will behave in the same manner as rapamycin in the extraction processes of this invention.

The neutral tricyclic macrolides rapamycin, 32-desmethylrapamycin, 15-deoxorapamycin and FK-506 are produced by fermentation of various strains of *Streptomyces* under the proper conditions and are neutral as there is no basic amino group or acidic phenolic or carboxyl groups present. Rapamycin is produced by culturing *S. hygroscopicus* NRRL 5491 in an aqueous medium. The fermentation broth may be extracted directly with an organic solvent or the mycelia containing the tricyclic macrolide are recovered from the growth medium and extracted with an organic solvent such as methanol to obtain a mixture comprised of the desired neutral tricyclic macrolide, related compounds, acidic compounds such as fatty acids, basic compounds such as alkaloids and peptides, and neutral lipophilic compounds such as fats. The fermentation broth may be acidified to help prevent or break up emulsions or establish an optimum fermentation environment. The proportions and types of impurities obtained along with the neutral macrolide in the fermentation broth extract may vary with the microorganism used, the fermentation conditions, and the nutrients used. For convenience, the fermentation broth extract is concentrated to facilitate transportation and/or storage until the macrolide can be isolated.

Isolation and purification of the tricyclic macrolides from the fermentation broth extract has been, before this invention, a laborious expensive process employing various chemical and chromatographic techniques to obtain purified material. [U.S. Pat. No. 5,091,389; 3,993,749; WO 93/11130; Sehgal, J. of Antibiotics 28(10)727(1975)]. The fermentation broth extract concentrate for rapamycin contains only 5 to 15% rapamycin and up to about 50% acidic components, for example, and rapamycin must be separated from the other components. Typically, processes for recovery of the tricyclic macrolides from fermentation broth extracts involves adsorption on and desorption from activated carbon, selective solubility procedures, and one or more time consuming and expensive chromatographic procedures using column chromatography and/or high pressure liquid chromatography. Heretofore, acidic or basic conditions have been avoided in separating a neutral macrolide from the impurities present in the fermentation broth extract as tricyclic macrolides, such as rapamycin, are considered to be unstable under acidic or basic conditions. Rapamycin in water-miscible solution, i.e., in methanol or tetrahydrofuran, undergoes degradation by inorganic bases such as aqueous sodium hydroxide, organic bases such as 4-dimethylaminopyridine (DMAP) or 1,8-diazobicyclo[5.4.0]undec-7-ene (DBU) or aqueous mineral acids such as hydrochloric acid and Lewis acids such as zinc chloride [Steffan et al., Tetrahedron Letters 34(23), 3699–3702 (1993), D. Yohanes and S. J. Danishefsky, Tetrahedron Letters 33(49), 7469–7472 (1992); Luengo et al., Tetrahedron Letters 34(6), 991–994 (1993) and D. Yohannes et al., Tetrahedron Letters 34(13), 2075–2078 (1993)].

This invention provides a relatively fast and efficient process for recovery of a neutral macrolide, especially a tricyclic macrolide, and more specifically rapamycin, from fermentation broth extract concentrates and mother liquors or concentrates thereof containing a neutral macrolide recovered from recrystallization solvents, triturations and product washings and avoids the time consuming and expensive chromatographic separations exemplified in U.S. Pat. No. 5,091,389; 3,993,749; WO 93/11130; and Sehgal, J. of Antibiotics 28(10)727(1975). The process comprises separation of the acidic and/or basic components from the neutral components by first dissolving the macrolide-containing concentrate in a suitable water-immiscible solvent, extracting the acidic and/or basic components into aqueous base or acid respectively, and employing selective solubility or extraction techniques to separate the neutral polar tricyclic macrolide from the non-polar neutral materials present in the concentrate. While the process described herein refers to concentrates of fermentation broth extracts or mother liquors obtained from macrolide isolation procedures from fermentation broth concentrate, the whole extract solution or mother liquor solutions can be used in the process of this invention provided the solvent or solvent mixture used for the fermentation broth extraction or recrystallization, trituration or washings is amenable to the process and the volume of the solvent is not cumbersome. Solvent volume may be reduced by partial concentration. Any of the solutions to which the process of this invention may be applied may be referred to as a macrolide containing concentrate.

The product obtained by said process can be purified to acceptable purity by standard procedures known to those skilled in the art.

The process of this invention is outlined in the Scheme 1 below. In the following disclosure of the invention process, a non-polar solvent is a non-aromatic hydrocarbon solvent such as cyclohexane, cyclohexene, hexane, heptane, penlane and the like. Solvents which are immiscible with the non-aromatic hydrocarbon solvent include but are not limited to acetonitrile and dimethylformamide. The term extraction refers to the procedure of thoroughly mixing a first solution or solvent with a second solution or solvent, immiscible with said first solution or solvent, allowing the immiscible solutions to separate one from the other and physically removing one layer or phase from the other wherein a component in one solution is transferred to the other solution or solvent. The term wash when referring to a solution refers to the extraction procedure and when referring to a solid, means to rinse the solid with a solvent in which the solid is substantially insoluble. The term mother liquor refers to the organic solvent solutions obtained from crystallization filtrates, washings and back extractions of aqueous extracts and washings and triturations of collected solids. A macrolide solvent is a solvent or solvent mixture which will dissolve the macrolide and accompanying impurities such as the acidic or basic components. A macrolide non-solvent is a solvent or solvent mixture in which the macrolide is substantially insoluble but one in which neutral components such as fats are soluble. A macrolide crystallizing solvent is a solvent or solvent mixture from which the macrolide can be recrystallized or crystallized from an amorphous state upon trituration. Where the process requires the concentration of a solution, it is preferred that the solvent or solvent mixture have sufficient volatility so as to distill off under non-degrading temperature and pressure conditions.

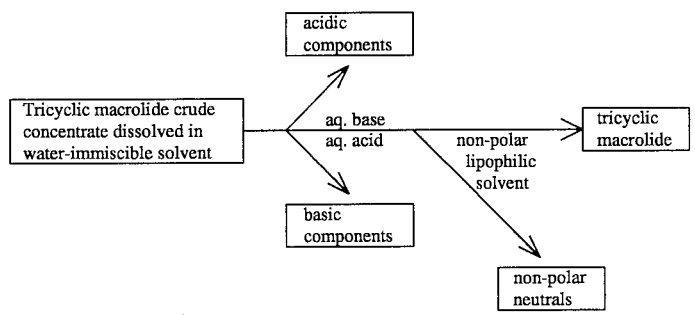

Scheme 1.

According to the process, the concentrate containing the macrolide, whether from fermentation broth extract concentrate or concentrates from recrystallization and/or wash solvents, is dissolved in a water-immiscible solvent or solvent mixture selected for the ability to dissolve the concentrate and ease of removal, including but not limited to dichloromethane, t-butyl methyl ether, ethyl acetate, toluene, 1-butanol, an ethyl acetate/toluene mixture, a heptane/ethyl acetate mixture, or a hexane/methylene chloride mixture. Aqueous solutions of base, including sodium hydroxide, sodium bicarbonate, sodium carbonate, ammonium hydroxide and the like, preferably sodium hydroxide, in concentrations ranging from 0.1 to 5N, suitably from 0.1 to 1.0N, are particularly useful for extracting the acidic components. Organic bases such as triethylamine are not as effective as the stronger aqueous inorganic bases in removing the acidic components. Aqueous solutions of mineral acid, including hydrochloric acid, monopotassium phosphate, monosodium sulfate and the like, preferably hydrochloric acid, in concentrations of from 0.1 to 5N, suitably 0.1 to 1.0N, are particularly useful for extracting the basic components. Organic acids, such as trifluoroacetic acid are not as effective as the mineral acids in removing the basic components. Extractions of acidic and/or basic components from the solution containing the macrolide are conveniently performed between about −5° C. and 45° C., suitably in the range of about −5° to 30° C. The extraction process temperature limitations are, of course, governed by the freezing and boiling points of the solvents used. To avoid possible degradation of the macrolide by the acid or base, the extraction process should be completed without delay. Depending on the amounts of acidic and/or basic components present, extraction of the acidic components alone or basic components alone may be sufficient in removal of enough impurity from the macrolide containing solution to permit isolation of the tricyclic macrolide.

It is advantageous to remove the acidic (or basic) components from the solution of macrolide-containing concentrate in one time-saving extraction step. The amount of aqueous base (or acid) needed so that excess base (or acid) is available in the extraction process can be determined by extracting an aliquot taken from the solution of the macrolide containing concentrate with aqueous base (or acid) and determining the volume of aqueous base (or acid) required to give an extract of the fermentation concentrate solution aliquot having a pH such that a stoichimetric excess of base (or acid) is available. The excess of acid or base is determined by using a pH meter or other means of determining pH. The volume of aqueous base (or acid) needed to extract the solution from which the aliquot was taken is then proportional to the ratio of the volumes of neutral macrolide containing solution to be extracted and the aliquot taken therefrom. Thus extraction of acidic (or basic) components can advantageously be done in one operation rather than performing multiple extractions with less that sufficient amounts of aqueous base (or acid). Obviously where both acidic and basic components are to be removed from the solution of the macrolide containing concentrate, separate extractions with aqueous base and aqueous acid respectively will have to be performed. With solutions of rapamycin-containing concentrate, for example, one extraction with aqueous sodium hydroxide solution sufficient to have a final pH of 12 is sufficient to remove substantially all of the acidic components.

After performing the extraction procedures to remove the acidic and/or basic components from the water-immiscible solvent solution containing the macrolide, the macrolide may be separated from the non-polar neutral components by one of the following methods:

(1) The macrolide containing water-immiscible solvent solution from which the acidic and/or basic components were extracted, is treated with a macrolide non-solvent in sufficient quantity so as to render the macrolide and perhaps macrolide-related products insoluble in the resulting solution and form a separate phase, either an oil or a solid, which may then be separated by ordinary separation techniques known to those skilled in the art.

(2) The water-immiscible solvent macrolide-containing solution from which the acidic and/or polar components were extracted is concentrated and the residual material containing the macrolide is dissolved in a macrolide dissolving solvent such as acetonitrile or dimethylformamide and extracted with an immiscible non-aromatic hydrocarbon solvent such as cyclohexane, hexane, heptane or cyclohexene. The macrolide-dissolving solvent layer is separated and concentrated. The residue containing the macrolide is then triturated with a crystallizing solvent to obtain the macrolide if said macrolide is a solid or purified by techniques known to those skilled in the art such as chromatography if the macrolide is an oil. Alternatively, the macrolide-dissolving solvent, after extraction with the non-aromatic hydrocarbon solvent may be treated with a miscible non-macrolide dissolving solvent as in procedure (1) above.

(3) The macrolide containing water-immiscible solvent solution from which the acidic and/or basic components were extracted is concentrated and the residual material is triturated with macrolide crystallizing solvent such as diethyl ether, diisopropyl ether or t-butyl methyl ether.

Alternatively, the macrolide containing concentrate can be extracted first according to one of methods (1) to (3) above to remove non-polar components and then the residue containing the macrolide dissolved in a water-immiscible solvent if not already in such a solvent and extracted with aqueous base and/or acid to remove the acidic and/or basic components.

The macrolide recovered from solution using the above processes can be purified to the degree of purity desired by conventional purification techniques known to those skilled in the art. The filtrates and washings may be reworked to recover additional macrolide if desired.

The above process takes advantage of the unexpected finding that rapamycin does not decompose when subjected to aqueous acid or base extraction procedures from water-immiscible solvent solutions of macrolide containing concentrates under non-degrading conditions. It was previously thought that degradation of rapamycin would occur, based on the observed degradation of rapamycin that occurs in acidic or basic solution. The extraction process of this invention greatly shortens the time necessary to recover macrolides from said concentrates and avoids the time-consuming and expensive chromatographic processes previously disclosed.

The following examples are merely illustrative of the process of the present invention in isolating rapamycin from fermentation broth and mother liquor concentrates and are not to be construed as limiting the scope of this invention in any way. In the following examples, the identity of the product isolated was confirmed as rapamycin through comparison of physical, spectral and chromatographic properties to those of authentic rapamycin. The purity of the product (unrecrystallized) was determined by high pressure liquid chromatographic analysis.

EXAMPLE 1

A solution of concentrated fermentation broth extract (157.0 g, 10.4% rapamycin content) taken up in methylene chloride (600 mL) was washed with three 150 mL portions of 0.5N NaOH solution at 0°–5° C., washed with water until the wash is neutral, and then washed with brine. The methylene chloride solution was concentrated and the residue (70.5 g) triturated with diethyl ether (140 mL). The crystalline solid was collected, washed with diethyl ether and dried to obtain rapamycin (6.3 g, 91.7% purity, 35.4% yield). Concentration of the diethyl ether filtrates gave 63.5 g of oil having a 13.1% rapamycin content.

EXAMPLE 2

A solution of concentrated fermentation broth extract (206.0 g, 11.8% rapamycin content) was taken up in t-butyl methyl ether (800 mL) and washed with three 400 mL portions of 0.5N NaOH solution at 0°–5° C. and then washed with water until the wash was neutral. The t-butyl methyl ether solution was concentrated and the residue (75.0 g) triturated with diethyl ether (150 mL). The crystalline solid was collected, washed with diethyl ether, and dried to obtain rapamycin (11.4 g, 92.2% purity, 43.3% yield). Concentration of the diethyl ether filtrates gave 58.7 g of oil having a 11.3% rapamycin content.

EXAMPLE 3

A solution of concentrated fermentation broth extract (10.58 g, 10.4% rapamycin content) taken up in acetonitrile (23 mL) was washed with two 23 mL portions of cyclohexane and then concentrated. The residue was dissolved in dichloromethane and washed sequentially with three 23 mL portions of 0.5N NaOH solution at 0°–5° C., two 23 mL portions of 0.5N HCl at 0°–5° C., and then with water until the wash was neutral. The dichloromethane solution was concentrated and the residue (4.07 g) triturated with diethyl ether. The crystalline solid was collected, washed with diethyl ether, and dried to give rapamycin (0.64 g, 89.5% purity, 58.2% yield). The diethyl ether filtrates were concentrated to obtain 3.36 g of oil having a 9.8% rapamycin content.

EXAMPLE 4

A solution of concentrated fermentation broth extract (100.0 g, 11.8% rapamycin content) taken up in ethyl acetate (400 mL) was washed with one 200 mL portion and two 100 mL portions of 0.5N NaOH solution at 0°–5° C. and then washed with two 200 mL portions of 0.5N hydrochloric acid solution at 0°–5° C. and finally washed with water until the wash was neutral. The aqueous washings were back extracted with ethyl acetate (100 mL) and the ethyl acetate solutions combined. The ethyl acetate solution was concentrated and the residue (43.2 g) triturated with diisopropyl ether (45 mL). The crystalline solid was collected, washed with diisopropyl ether and dried to yield 9.5 g of rapamycin (85.3% purity, 68.7% yield). The diisopropyl ether filtrates were concentrated to give an oil (31.6 g) with a 6.6% rapamycin content.

EXAMPLE 5

A solution of concentrated fermentation broth extract (25.2 g, 10.4% rapamycin content) taken up in a mixture of toluene (120 mL) and ethyl acetate (25 mL) was washed sequentially with three 50 mL portions of 0.5N NaOH solution at 0°–5° C., twice with two 50 mL portions of 0.5N hydrochloric acid at 0°–5° C., and then with water until the wash was neutral. The toluene/ethyl acetate solution (128 mL) was divided into two equal portions for further treatment by the following methods:

Method A. The toluene/ethyl acetate solution (64 mL) was concentrated and the residue (5.7 g) triturated with diethyl ether (11 mL). The crystalline solid was collected, washed with additional diethyl ether, and dried to give 0.84 g of rapamycin (92.7% purity, 64.1% yield). Concentration of the diethyl ether filtrates gave 4.3 g of an oil having a 6.8% rapamycin content.

Method B. The toluene/ethyl acetate solution (64 mL) was concentrated and the residue (9.0 g) was dissolved in acetonitrile (50 mL). The acetonitrile solution was washed with two 25 mL portions of cyclohexane. The acetonitrile solution was then concentrated and the residue (4.3 g) triturated with diethyl ether (11 mL). The crystalline solid was collected, washed with diethyl ether, and dried to yield 0.81 g of rapamycin (94.6% purity, 61.8% yield). Concentrations of the diethyl ether filtrates gave 3.0 g of an oil having a 5.9% rapamycin content.

EXAMPLE 6

Mother liquor concentrate (996.0 g, 21.6% rapamycin content) was triturated with t-butyl methyl ether (4000 mL). The crystalline solids were collected, washed with t-butyl methyl ether (500 mL), and dried to yield 36.2 g of rapamycin (95.1% purity, 13.8% yield). The filtrates were washed with one 2000 mL portion and two 1000 mL portions of 0.5N sodium hydroxide solution at 0°–5° C. The combined base extract was washed once with t-butyl methyl ether (500 mL). The t-butyl methyl ether filtrate and extract were combined and washed with water until the wash was neutral. The water extracts were combined and extracted with t-butyl methyl ether (500 mL). The t-butyl methyl ether solutions were combined, concentrated, and the residue (377.1 g) triturated with diisopropyl ether (350 mL). The crystalline solids were collected, washed with diisopropyl ether, and dried to give 126.7 g of rapamycin (82.4% purity, 58.9% yield). Thus the total recovery of rapamycin from the mother liquor concentrate was 162.9 g (72.7%). Concentration of the diisopropyl ether filtrates gave 157.9 g of oil having a 20.9% rapamycin content.

EXAMPLE 7

A solution of mother liquor concentrate (562.1 g, 21.6% rapamycin content) taken up in dichloromethane (2000 mL) was washed with three 500 ml portions of 0.5N sodium hydroxide solution at 0°–5° C. and the combined aqueous basic extracts were extracted with one 200 mL portion of dichloromethane. The organic solutions were combined and washed with two 500 mL portions of 0.5N hydrochloric acid solution at 0°–5° C. The combined aqueous acid extracts were extracted with one 200 mL portion of dichloromethane. The combined organic extracts were washed with water until the wash water was neutral. The organic solution was concentrated and the residue (255.0 g) was triturated with diisopropyl ether (250 mL). The crystalline solids were collected, washed with diisopropyl ether and dried to give 108.6 g of rapamycin (86.6% purity, 77.4% recovery). Concentration of the diisopropyl ether filtrates gave 100.2 g of oil having a 23.1% rapamycin content.

EXAMPLE 8

Aqueous 0.5N sodium hydroxide (400 mL) at 0°–5° C. was added to a vigorously stirred chilled (0°–5° C.) solution of concentrated fermentation broth extract (198.5 g, 8.3% rapamycin content) taken up in 800 mL of t-butyl methyl ether at such a rate so that the temperature could be maintained at 0°–5° C. After vigorous stirring for 5 minutes, the lower aqueous basic layer was removed and stored at 0°–5° C. The organic layer was re-extracted with two 200 mL portions of 0.5N sodium hydroxide solution at 0°–5° C. The aqueous basic extracts were combined and re-extracted with t-butyl methyl ether (200 mL). The t-butyl methyl ether solutions were combined and washed with water until the wash was neutral (pH 7). The aqueous washes were combined and extracted with t-butyl methyl ether (100 mL). The t-butyl methyl ether solutions were combined, washed with saturated aqueous sodium chloride solution, and concentrated under vacuum at 40° C. The residue was triturated with diisopropyl ether (85 mL) at 20°–250° C. for a minimum of one hour and the mixture cooled to 0°–5° C. overnight. The crystalline solid was collected using a sintered glass Buchner funnel and washed with a 4:1 mixture of diisopropyl ether - t-butyl methyl ether at 20°–25° C. (5×20 mL or until filtrate was colorless). The crystalline solid is dried to constant weight to yield 12.0 g of rapamycin (91.2% purity, 66.4% recovery). Concentration of the t-butyl methyl ether filtrates and washing gave 63.9 g of a gum having a 3.63% rapamycin content.

EXAMPLE 9

Mother liquor concentrate (200 g, 25% rapamycin content) was dissolved with stirring in t-butyl methyl ether (800 mL) at room temperature. The stirred solution was cooled to 0°–5° C. and extracted without delay with 270 mL of 0.65 N sodium hydroxide solution, precooled to 0°–5° C., while maintaining the temperature of the mixture at 0°–5° C. (The amount of aqueous sodium hydroxide necessary to have a final pH of 12 in the extract was determined on an aliquot of the concentrated mother liquor.)

The aqueous base layer was stored at 0°–5° C. while the organic layer was washed with 5% sodium chloride solution while maintaining the mixture at 0°–5° C. The aqueous basic extract was back extracted with t-butyl methyl ether (100 mL). The organic layers were combined and washed with three 200 mL portions of 5% sodium chloride solution (pH of final wash solution was 7.4). The organic solution was concentrated under reduced pressure (60–130 mmHg) at a temperature of 25°–40° C. Cyclohexene (80 mL) was added slowly over 30 minutes to the residue with stirring at room temperature and stirred until crystallization was complete (3 hours). The mixture was stirred at room temperature for one hour more and the mixture chilled to 0°–5° C. and stirred overnight. The off-white crystalline solid was then collected on a fritted glass Buchner funnel. The solid was washed five times with 40 mL portions of a 2:3 mixture of t-butyl methyl ether and cyclohexene. The solid was dried to constant weight in a vacuum oven at 35°–40° C. to obtain 22.7 g of rapamycin (90.6% pure, 41.4% recovery). Concentration of the filtrates and washings (t-butyl methyl ether and cyclohexene) gave 60.1 g of an oil having a 37.5% rapamycin content.

What is claimed:

1. A process for separating a neutral non-polypeptide macrolide from acidic, basic and non-polar neutral impurities present in a concentrate of fermentation broth extracts or mother liquors containing said neutral macrolide which comprises in any order extraction step (a) and optionally one or both of steps (b) and (c) as follows:
   (a) a solution of said concentrate in a water-immiscible solvent is extracted with aqueous base to substantially remove all acidic impurities;
   (b) a solution of said concentrate in a water-immiscible solvent is extracted with aqueous acid to substantially remove all basic impurities;
   (c) a solution of said concentrate is treated with a non-aromatic hydrocarbon solvent to separate the non-polar neutral impurities from the neutral macrolide.

2. A process according to claim 1 wherein the non-polar neutral components of the neutral macrolide-containing fermentation broth extract concentrate or mother liquor concentrate are removed by extraction of a solution of said concentrate in a first solvent with a second non-aromatic hydrocarbon solvent immiscible with the first solvent and in which the neutral macrolide is insoluble.

3. A process according to claim 1 wherein the water-immiscible solution containing the neutral macrolide after extraction of acid and/or basic components is treated with a sufficient quantity of a miscible macrolide non-solvent to cause the macrolide to become insoluble in the resulting solvent mixture and thus separate from the solution whereby the neutral macrolide can be separated from the solvent mixture.

4. A process according to claim 1 wherein the water-immiscible solution containing the neutral macrolide after extraction of acidic and/or basic components is concentrated and the residue crystallized by admixture with a crystallizing solvent or solvent mixture.

5. A process according to claim 1 wherein the neutral macrolide is a tricyclic macrolide.

6. A process according to claim 5 wherein the neutral tricyclic macrolide is rapamycin or a naturally occurring homolog, analog or isomer thereof or FK-506 or a naturally occurring homolog, analog or isomer thereof.

7. A process according to claim 6 wherein the neutral tricyclic macrolide is rapamycin, 32-desmethylrapamycin or 15-deoxorapamycin.

8. A process according to claim 6 wherein the neutral tricyclic macrolide is rapamycin.

9. A process according to claim 6 wherein the neutral tricyclic macrolide is FK-506.

10. The process according to claim 1 wherein the extractions of steps (a) and/or (b) are performed at about −5° C. to about 45° C.

11. The process according to claim 10 wherein the extractions are performed at about −5° C. to about 30° C.

* * * * *